United States Patent [19]

Tully et al.

[11] Patent Number: 5,124,355

[45] Date of Patent: Jun. 23, 1992

[54] SYNERGISTIC MICROBIOCIDAL COMPOSITION OF 2-(DECYLTHIO)ETHANEAMINE AND 1,2-DIBROMO-2,4-DICYANOBUTANE

[75] Inventors: John C. Tully, Wauconda; Linda Young-Bandala, La Grange, both of Ill.

[73] Assignee: W. R. Grace & Co.-Conn., New York, N.Y.

[21] Appl. No.: 618,859

[22] Filed: Nov. 28, 1990

[51] Int. Cl.$^5$ .................. A01N 33/08; A01N 37/34
[52] U.S. Cl. .................................. 514/526; 514/665
[58] Field of Search ........................... 514/526, 665

[56] References Cited

U.S. PATENT DOCUMENTS

| | | | |
|---|---|---|---|
| 3,608,084 | 9/1971 | Matt | 514/526 |
| 3,833,731 | 9/1974 | Grier et al. | 514/526 |
| 3,873,597 | 3/1975 | Harmetz et al. | 260/465.7 |
| 3,877,922 | 4/1975 | Grier et al. | 71/67 |
| 3,929,858 | 12/1975 | Swigert | 260/465.7 |
| 4,442,122 | 4/1984 | Engelhart et al. | 71/67 |
| 4,816,061 | 3/1989 | Walter, Jr. et al. | 514/665 |
| 4,857,557 | 8/1989 | Donofrio et al. | 514/711 |
| 4,859,702 | 8/1989 | Whitekettle et al. | 514/520 |
| 4,859,705 | 8/1989 | Donofrio et al. | 514/600 |
| 4,859,708 | 8/1989 | Donofrio et al. | 514/727 |
| 4,863,960 | 9/1989 | Donofrio et al. | 514/526 |
| 4,914,130 | 4/1990 | Donofrio et al. | 514/634 |
| 4,916,123 | 4/1990 | Donofrio et al. | 514/75 |
| 4,916,158 | 4/1990 | Whitekettle et al. | 514/515 |
| 4,916,159 | 4/1990 | Whitekettle et al. | 514/528 |
| 4,916,164 | 4/1990 | Whitekettle et al. | 514/665 |

FOREIGN PATENT DOCUMENTS 61-103810  5/1986  Japan .

*Primary Examiner*—Allen J. Robinson
*Attorney, Agent, or Firm*—James P. Barr

[57] ABSTRACT

The present invention is directed to a combination of two types of biocidal materials that give rise to synergistic effects against microorganisms in aqueous systems such that the extent to which the microorganisms are killed exceeds that which one would expect from using the sum of the individual components of the composition. More specifically, this invention is directed to a combination comprising 2-(decylthio)ethaneamine and 1,2-dibromo-2,4-dicyanobutane in an amount effective to inhibit microbial growth. This combination has proven to be particularly effective in inhibiting the growth of *Enterobacter aerogenes* ATCC 13048 in aqueous systems.

6 Claims, No Drawings

SYNERGISTIC MICROBIOCIDAL COMPOSITION OF 2-(DECYLTHIO)ETHANEAMINE AND 1,2-DIBROMO-2,4-DICYANOBUTANE

BACKGROUND OF THE INVENTION

1. Field of the Invention

This invention relates to the treatment of aqueous systems and more particularly to biocidal materials that are synergistic against microorganisms typically found in industrial aqueous systems such as cooling water systems, air washer systems and pulp and paper mill systems.

2. Description of the Prior Art

The formation of slime by microorganisms is a problem that is encountered in many industrial aqueous systems. In industrial cooling water systems, for example, the water used is generally city water, and is sometimes untreated river water for large systems. As such, the water is not sterile, with the result that bacteria accumulate in the system. In addition, a significant portion of bacteria is entrained in the air as the system water cascades down the tower fill. This commonly gives rise to a slimy deposit on the surfaces of the system which come into direct contact with the cooling water. Both once-through and recirculating cooling systems employ large quantities of water as a cooling medium, in which formation of slime by microorganisms is an extensive and constant problem.

The slime formation not only aids in the deterioration of the tower structure in the case of wooden towers, but also may tend to clog up the equipment and make it less efficient if allowed to accumulate. Slime carried through the cooling system plugs and fouls lines, valves, strainers, etc. Bacteria carried through the system in the water deposits on surfaces such as heat exchanger surfaces to form slime masses which impede heat transfer and greatly reduce the efficiency of the cooling system. The slime deposits also provide an environment conducive to the growth of anaerobic bacteria which thrive in the low oxygen environment beneath the slime. These anerobic organisms can cause pitting and corrosion of metal surfaces.

In pulp and paper mill systems, slime formed by microorganisms is commonly encountered and causes fouling, plugging, or corrosion of the system. The slime also becomes entrained in the paper produced to cause breakouts on the paper machines, which results in work stoppages and the loss of production time. The slime is also responsible for unsightly blemishes in the final product, which result in rejects and wasted output.

The previously discussed problems have resulted in the extensive utilization of biocides in cooling water and in pulp and paper mill systems. A variety of materials have been used in such applications including chlorine, chlorinated phenols, organobromines, and various organo-sulfur compounds. All of these compounds are generally useful for this purpose but each is attended by a variety of impediments. For example, chlorination is limited both by its specific toxicity for slime-forming organisms at economic levels and by the tendency of chlorine to react, which results in the expenditure of the chlorine before its full biocidal function is achieved. Other biocides are attended by odor problems and hazards in respect to storage, use or handling which limit their utility. To date, no one compound or type of compound has achieved a clearly established predominance in respect to the applications discussed.

The use of biocides may involve the continuous or frequent addition to the systems being treated and may require addition to multiple points or zones within these systems.

SUMMARY OF THE INVENTION

It is an object of this invention to provide a novel biocidal composition to inhibit the growth of microorganisms in aqueous systems.

It is another object of this invention to provide a biocidal composition containing the combination of 2-(decylthio)ethaneamine and 1,2-dibromo-2,4-dicyanobutane which is synergistic against microorganisms in aqueous systems.

In accordance with this invention, there have been provided a biocidal composition and a method of use thereof comprising a mixture of 1,2-dibromo-2,4-dicyanobutane and 2-(decylthio)ethaneamine, and wherein the composition is added to an aqueous system in an amount effective to exhibit microbial growth.

DETAILED DESCRIPTION

The present invention is directed to a combination of two types of biocidal materials that give rise to synergistic effects against microorganisms in aqueous systems such that the extent to which the microorganisms are killed exceeds that which one would expect from using the sum of the individual components of the composition. More specifically, this invention is directed to a combination comprising 2-(decylthio)ethaneamine and 1,2-dibromo-2,4-dicyanobutane in an amount effective to inhibit microbial growth. This combination has proven to be particularly effective in inhibiting the growth of *Enterobacter aerogenes* ATCC 13048 in aqueous systems.

2-(decylthio)ethaneamine is manufactured by the Dow Chemical Company under the name DTEA or XU40304.O1L according to U.S. Pat. No. 4,816,061. 1,2-dibromo-2,4-dicyanobutane is manufactured by Merck Chemical Division by Calgon Corporation according to U.S. Pat. No.'s 3,833,731, 3,873,597, 3,877,922 and 3,929,858.

The biocidal compositions of this invention are generally most effective when added to an aqueous system having a pH greater than 7, preferably between 8 to 9. The individual biocide components of this composition may be added to the system individually or may be pre-mixed and are added in an amount effective to inhibit microbial growth. The 2-(decylthio)ethaneamine is generally added to the system in a concentration of 0.7 to 1.2 ppm while the 1,2-dibromo-2,4-dicyanobutane is generally added in a concentration range of 4.0 to 12.0 ppm. The total biocide concentration in the aqueous systems is generally in the range 5 to 14 ppm, and is preferably 5.2 to 13.2 ppm.

The following examples are provided to illustrate the invention in accordance with the principles of this invention, but are not to be construed as limiting the invention in any way except as indicated in the appended claims. All parts and percentages are by weight unless otherwise indicated.

EXAMPLE 1

Blends of 2-(decylthio)ethaneamine and 1,2-dibromo-2,4-dicyanobutane were evaluated for synergism against

*Enterobacter aerogenes ATCC #13048*. The results are as follows:

| 2-(decylthio) ethaneamine | | | 1,2-dibromo- 2,4-dicyanobutane | | | Synergy Index |
|---|---|---|---|---|---|---|
| A1 | A2 | A | B1 | B2 | B | |
| 0.70 | 2.00 | 0.35 | 10.0 | 20.0 | 0.50 | 0.85* |
| 0.70 | 2.00 | 0.35 | 20.0 | 20.0 | 1.00 | 1.35 |
| 0.70 | 2.00 | 0.35 | 30.0 | 20.0 | 1.50 | 1.85 |
| 0.70 | 2.00 | 0.35 | 60.0 | 20.0 | 3.00 | 3.35 |
| 1.50 | 2.00 | 0.75 | 10.0 | 20.0 | 0.50 | 1.25 |
| 1.50 | 2.00 | 0.75 | 20.0 | 20.0 | 1.00 | 1.75 |
| 1.50 | 2.00 | 0.75 | 30.0 | 20.0 | 1.50 | 2.25 |
| 1.50 | 2.00 | 0.75 | 60.0 | 20.0 | 3.00 | 3.75 |
| 2.00 | 2.00 | 1.00 | 10.0 | 20.0 | 0.50 | 1.50 |
| 2.00 | 2.00 | 1.00 | 20.0 | 20.0 | 1.00 | 2.00 |
| 2.00 | 2.00 | 1.00 | 30.0 | 20.0 | 1.50 | 2.50 |
| 2.00 | 2.00 | 1.00 | 60.0 | 20.0 | 3.00 | 4.00 |
| 4.00 | 2.00 | 2.00 | 10.0 | 20.0 | 0.50 | 2.50 |
| 4.00 | 2.00 | 2.00 | 20.0 | 20.0 | 1.00 | 3.00 |
| 4.00 | 2.00 | 2.00 | 30.0 | 20.0 | 1.50 | 3.50 |
| 4.00 | 2.00 | 2.00 | 60.0 | 20.0 | 3.00 | 5.00 |

Example 2

| 2-(decylthio) ethaneamine | | | 1,2-dibromo- 2,4-dicyanobutane | | | Synergy Index |
|---|---|---|---|---|---|---|
| A1 | A2 | A | B1 | B2 | B | |
| 0.60 | 2.00 | 0.30 | 4.0 | 30.0 | 0.13 | IBR |
| 0.60 | 2.00 | 0.30 | 8.0 | 30.0 | 0.27 | IBR |
| 0.60 | 2.00 | 0.30 | 12.0 | 30.0 | 0.40 | IBR |
| 0.80 | 2.00 | 0.40 | 4.0 | 30.0 | 0.13 | IBR |
| 0.80 | 2.00 | 0.40 | 8.0 | 30.0 | 0.27 | 0.67* |
| 0.80 | 2.00 | 0.40 | 12.0 | 30.0 | 0.40 | 0.80* |
| 1.20 | 2.00 | 0.60 | 4.0 | 30.0 | 0.13 | 0.73* |
| 1.20 | 2.00 | 0.60 | 8.0 | 30.0 | 0.13 | 0.87* |
| 1.20 | 2.00 | 0.60 | 12.0 | 30.0 | 0.13 | 1.00 |

EXAMPLE LEGEND

Synergy Index $= A + B$

Where:
$A = A1/A2$
$B = B1/B2$

Where:
A1 = Concentration of 2-(decylthio)ethaneamine (ppm AI) in mixture
A2 = MIC endpoint of 2-(decylthio)ethaneamine
B1 = Concentration of 1,2-dibromo-2,4-dicyanobutane (ppm AI) in mixture
B2 = MIC endpoint of 1,2-dibromo-2,4dicyanobutane When:
$A + B = 1$ The combination is additive
$A + B > 1$ The combination is antagonistic
$A + B < 1$ The combination is synergistic Note: * = Synergy IBR = Insignificant Bacterial Reduction MIC = Minimum Inhibitory Concentration ppm AI = Parts per million - Active ingredients

We claim:

1. A microbiocidal composition comprising a synergistic mixture of 2-(dicylthio)ethaneamine and 1,2-dibromo-2,4-dicyanobutane in an amount effective to inhibit microbial growth wherein the 2-(dicylthio)ethaneamine and 1,2-dibromo-2,4-dicyanobutane are in a weight ratio of 0.7–1.2:4–12 respectively.

2. A method of inhibiting the growth of bacteria in aqueous systems comprising adding to the system a composition comprising a synergistic effective amount to inhibit the growth of bacteria, of a mixture of 2-(dicylthio) ethaneamine and 1,2-dibromo-2,4-dicyanobutane in a weight ratio of 7–1.2:4–12 respectively.

3. The method according to claim 2 wherein the aqueous system is maintained at a pH greater than 7.

4. The method according to claim 2 wherein the aqueous system is maintained at a pH between 8 and 9.

5. The method according to claim 2 wherein the aqueous system is a cooling water system.

6. The method according to claim 2 wherein the aqueous system is a pulp and paper making system.

* * * * *